United States Patent [19]

Halloran et al.

[11] Patent Number: 5,290,545
[45] Date of Patent: Mar. 1, 1994

[54] HAIR TREATMENT WITH BLENDED SILICONES

[75] Inventors: Daniel J. Halloran; Scott A. Daunheimer, both of Midland, Mich.

[73] Assignee: Dow Corning Corporation, Midland, Mich.

[21] Appl. No.: 897,639

[22] Filed: Jun. 12, 1992

[51] Int. Cl.$^5$ .......................... A61K 7/06; A61K 7/09
[52] U.S. Cl. ........................................ 424/70; 424/71
[58] Field of Search ..................... 424/70, 71; 524/262

[56] References Cited

U.S. PATENT DOCUMENTS

| | | |
|---|---|---|
| 4,559,227 | 12/1985 | Chandra et al. .................... 424/70 |
| 4,704,272 | 11/1987 | Oh et al. ............................. 424/70 |
| 5,100,657 | 3/1992 | Anther-Johnson et al. .......... 424/70 |
| 5,106,609 | 4/1992 | Bolich, Jr. et al. ................. 424/71 |
| 5,160,449 | 11/1992 | Halloran ............................. 424/70 |

*Primary Examiner*—Thurman K. Page
*Assistant Examiner*—Peter F. Kulkosky
*Attorney, Agent, or Firm*—James L. Decesare

[57] ABSTRACT

A cosmetic composition for use in the treatment of hair. The cosmetic composition contains a conditioning agent and the improvement resides in the conditioning agent being a mixture of (i) a polydiorganosiloxane gum and (ii) an amine functional siloxane polymer. A method of treating hair is also described in which the mixture is applied to hair for the purpose of improving wet and dry combing and imparting durable conditioning benefits to the hair.

4 Claims, No Drawings

HAIR TREATMENT WITH BLENDED SILICONES

BACKGROUND OF THE INVENTION

This invention is directed to the treatment of hair with a composition which includes the combination of a silicone gum and an amine function polysiloxane fluid. Such blends have been found to impart conditioning benefits to the hair.

Hair preparations are compositions which are employed on the scalp or hair. The most important hair preparations are shampoos, conditioning products, colorants, hairstyling preparations including setting lotions and hairsprays, and permanent wave preparations.

Shampoos are mild cosmetic products for cleaning the hair and scalp. Hair becomes soiled due to skin flakes, sebum, perspiration, dust, and residues from sprays, lotions and conditioning agents. Shampoos are designed to leave the hair clean, pliable, lustrous, possessing a pleasant odor, and easy to untangle, comb, manage, and style. The principal ingredient of a shampoo is a surfactant which functions to release dirt from the hair and to transport it to the aqueous medium. Since consumers equate lathering with cleanliness, anionic surfactants such as alkyl sulfates and sulfonates are preferred because of their high lather. Numerous other constituents are included in shampoos such as thickeners to prevent the shampoo from running down the face into the eyes, opacifiers to provide a rich pleasing pearlescent appearance, buffers to adjust the pH of the shampoo to a value which is gentle to the skin, and fragrances to impart a pleasant aroma to the washed hair following rinsing. Most frequently, shampoos are marketed as clear products although gels having a higher viscosity and packaged in tubes, and pearlescent compositions are available.

With the advent of consumer trends toward daily hair washing, conditioning shampoos have emerged which are designed to render the hair easy to comb and tangle free in the wet state, as well as glossy and soft when dry. Such conditioning is provided by the inclusion in the shampoo of a cationic polymer which upon rinsing produces a thin film on the hair. This film functions as a lubricant when the hair is wet and prevents static charge and "flyaway" when the hair is dry.

Conditioning may also be provided by hair conditioning products designed solely for that purpose such as rinses, mousses, aerosols, and pump sprays, which conditioners are applied following shampooing. These conditioning products are rinsed from the hair a short time following their application. Such conditioners prevent excessive split ends and other mechanical hair damage and roughening, and seek to neutralize the adverse effects which hair undergoes due to humidity, temperature, exposure to sunlight, frequent washing, combing, and brushing, and cosmetic treatments such as bleaching, dyeing, and waving.

It is known in the art to employ an amine functional silicone fluid in a hair conditioning shampoo as shown in U.S. Pat. No. 4,559,227 issued Dec. 17, 1985. It is also known in the art to employ silicone gums in hair conditioning shampoos as shown in U.S. Pat. No. 4,704,272 issued Nov. 3, 1987. What is not taught by the prior art and what constitutes the novel feature of the present invention is the use of a blend of both an amine functional silicone fluid and a silicone gum in the treatment of hair.

While silicone gums and non-polar fluids such as polydimethylsiloxanes have been shown to provide effective conditioning benefits to hair, the conditioning effect is relatively non-substantive. According to the present invention, this disadvantage is overcome by blending the silicone gum with a silicone having polar amine groups along the siloxane chain. Such blends have much improved deposition properties versus blends of silicone gums with non-polar fluids. Not only do the blends of the present invention improve wet combing, but they impart durable and long-lasting conditioning benefits. Further, the blends are low in viscosity with the result that pumping and mixing are facilitated.

SUMMARY OF THE INVENTION

The invention is directed to the treatment of hair with a cosmetic composition which includes as a conditioning agent for the hair a mixture of a silicone gum and an amine functional silicone. Such mixtures have been found to improve the wet combing characteristics of hair while at the same time providing durable conditioning effects.

The invention is also directed to a composition in the form of a mixture of the silicone gum and the amine functional silicone, which mixture is of general application in the personal care field including treatment of the hair and skin. Aesthetically, the mixture rubs-on "tacky" but will rub-out to a smooth soft feel. Such perception is of importance in the consumer oriented personal care market.

These and other features, objects, and advantages, of the herein defined present invention will become more apparent from a consideration of the following detailed description thereof.

DETAILED DESCRIPTION OF THE INVENTION

The amine functional siloxane polymer employed in the blends in accordance with the present invention has the formula:

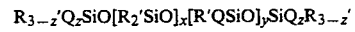

$$R_{3-z'}Q_zSiO[R_2'SiO]_x[R'QSiO]_ySiQ_zR_{3-z'}$$

wherein R' denotes an alkyl group of 1 to 4 carbons or a phenyl group with the proviso that at least 50 percent of the total number of R' groups are methyl; Q denotes an amine functional substituent of the formula —R"Z wherein R" is a divalent alkylene radical of 3 to 6 carbon atoms and Z is a monovalent radical selected from the group consisting of —NR$_2$''', and —NR'''(CH$_2$)$_n$NR$_2$''''; wherein R''' denotes hydrogen or an alkyl group of 1 to 4 carbons, R'''' denotes an alkyl group of 1 to 4 carbons, and n is a positive integer having a value of from 2 to 6; z has a value of 0 or 1; x has an average value of 25 to 3000; y has an average value of 0 to 100 when z is 1, y has an average value of 1 to 100 when z is 0; with the proviso that in all cases y has an average value that is not greater than one tenth the average value of x.

Suitable R' groups are represented by and may be independently selected from among methyl, ethyl, propyl, isopropyl, butyl, isobutyl, and phenyl, with the proviso that at least fifty percent of the R' groups are methyl.

The alkylene radicals represented by R" may include trimethylene, tetramethylene, pentamethylene, —CH$_2$CHCH$_3$CH$_2$—, and —CH$_2$CH$_2$CHCH$_3$CH$_2$—.

Siloxanes where R" is a trimethylene or an alkyl substituted trimethylene radical such as —CH₂CHCH₃CH₂—, are preferred.

Alkyl groups of 1 to 4 carbon atoms as represented by R''' and R'''' include methyl, ethyl, propyl, isopropyl, butyl, and isobutyl.

Useful Z radicals include the unsubstituted amine radical —NH₂, alkyl substituted amine radicals such as —NHCH₃, —NHCH₂CH₂CH₂CH₃, and —N(CH₂CH₃)₂; and aminoalkyl substituted amine radicals such as —NHCH₂CH₂NH₂, —NH(CH₂)₆NH₂, and —NHCH₂CH₂CH₂N(CH₃)₂.

When z is zero, the silicone polymer has only pendent amine functional substituents in the polymer chain. When z is one, the silicone polymer may have only terminal amine functional substituents or both terminal and pendent amine functional substituents in the polymer chain. Preferably, x may vary from a value of 25 to 100, and y may vary from zero to 100 when z is one and from one to 100 when z is zero. Most preferably, the value of x+y is in the range of about 50 to 500.

The polydiorganosiloxane gum suitable for use in the present invention are polydimethylsiloxane gums which can be represented by an average unit formula

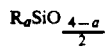

$$R_a SiO_{\frac{4-a}{2}}$$

where each R is a methyl radical, a vinyl radical, a phenyl radical, an ethyl radical or a 3,3,3-trifluoropropyl radical and a has an average value of 1.95 to 2.005 inclusive. Since the polydiorganosiloxane gums are essentially polydimethylsiloxane gums, at least 90 percent of the total R groups are methyl radicals and the remaining R groups are vinyl, phenyl, ethyl of 3,3,3-trifluoropropyl. Small amounts of other groups can be present such as 1 or 2 percent of the total R, where such groups are other monovalent hydrocarbon groups, such as propyl, butyl, hexyl, cyclohexyl, beta-phenylethyl, octadecyl and the like; other halogenated monovalent hydrocarbon radicals, such as chloromethyl, bromophenyl, α,α,α-trifluorotolyl, perfluoroheptylethyl, dichlorophenyl and the like; cyanoalkyl; alkoxy, such as, methoxy, propoxy, ethoxy, hexoxy and the like; ketoxime; halogen; hydroxyl; and acyloxy. The groups which are present in small amounts are considered as incidental and not producing any significant characteristic changes of the polydimethylsiloxane gum.

The polydiorganosiloxane gums suitable for the present invention are essentially composed of dimethylsiloxane units with the other units being represented by monomethylsiloxane, trimethylsiloxane, methylvinylsiloxane, methylethylsiloxane, diethylsiloxane, methylphenylsiloxane, diphenylsiloxane, ethylphenylsiloxane, vinylethylsiloxane, phenylvinylsiloxane, 3,3,3-trifluoropropylmethylsiloxane, dimethylphenylsiloxane, methylphenylvinylsiloxane, dimethylethylsiloxane, 3,3,3-trifluoropropyldimethylsiloxane, mono-3,3,3-trifluoropropylsiloxane, monophenylsiloxane, monovinylsiloxane and the like.

The polydiorganosiloxane gums are well known in the art and can be obtained commercially, and are considered to be insoluble polydiorganosiloxanes which have viscosities greater than 1,000,000 cs. at 25° C., preferably greater than 5,000,000 cs. at 25° C.

These gums may be used alone as well as in admixture with one or more volatile ingredients such as a cyclic silicone. Volatile cyclic silicones which may be employed are polydimethylcyclosiloxanes exemplary of which are octamethylcyclotetrasiloxane and decamethylcyclopentasiloxane. The viscosity at 25° C. of the volatile cyclics is generally of the order of 2.5 to 6.0 cs. Such volatile ingredients are generally represented by the formula $(CH_3)_2SiO_x$ where x is 3–8. When used in admixture with the gum, the level of the cyclic is generally of the order of about thirteen percent by weight.

The compositions of this invention may contain a surfactant selected from the group consisting of anionic and amphoteric surfactants. The surfactant system should provide an acceptable level of foam on the hair and be capable of cleaning the hair, and may comprise one or more water soluble detergents, i.e., an anionic or amphoteric surfactant. Suitable anionic detergents include sulfonated and sulfated alkyl, aralkyl and alkaryl anionic detergents; alkyl succinates; alkyl sulfosuccinates and N-alkyl sarcosinates. Especially preferred are the sodium, magnesium, ammonium, and the mono-, di- and triethanolamine salts of alkyl and aralkyl sulfates as well as the salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic detergents include, among others, sodium lauryl sulfate, sodium lauryl ether sulfate, ammonium lauryl sulfate, triethanolamine lauryl sulfate, sodium C14–16 olefin sulfonate, ammonium pareth-25 sulfate (ammonium salt of a sulfated polyethylene glycol ether of a mixture of synthetic C12–15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine, ammonium and sodium lauryl sulfates. Sodium lauryl ether sulfate is also very suitable for use in the compositions of this invention.

Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500. Particularly preferred amphoteric surfactants are the substituted quaternary hydroxy cycloimidinic acid alkali metal alcoholates described in U.S. Pat. No. 2,528,378.

The most preferred of the amphoteric surfactants are the substituted quaternary hydroxy cycloimidinic acid alkali metal alkoxymethyl carboxylates described in U.S. Pat. No. 2,781,354. The betaines may have the structure:

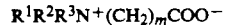

$$R^1R^2R^3N^+(CH_2)_mCOO^-$$

wherein $R^1$ is an alkyl group having about 12 to 18 carbon atoms or a mixture thereof, $R^2$ and $R^3$ are independently lower alkyl groups having 1 to 3 carbon atoms, and m is an integer from 1 to 4. Specific betaines useful in the products of the invention are for example alpha-(tetradecyldimethylammonio)acetate, beta-(hexadecyldiethylammonio)propionate, and gamma-(dodecyldimethylammonio)butyrate.

The sultaines may have the structure:

$$R^1R^2R^3N^+(CH_2)_mSO_3^-$$

wherein $R^1$, $R^2$, $R^3$, and m are defined as above. Specific useful sultaines are for example 3-(dodecyldimethylammonio)-propane-1-sulfonate, and 3-(tetradecyldimethylammonio)ethane-1-sulfonate.

The compositions of this invention may contain a nonionic surfactant. The nonionic surfactants of the present invention are selected from the group consisting of fatty acid alkanolamide and amine oxide surfactants. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, for example, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are well known nonionic surfactants usually obtained by oxidizing a tertiary amine to form the amine oxide. They are sometimes also referred to as polar nonionic surfactants. Amine oxide surfactants include, for example, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms.

For purposes of this invention the alkanolamide and amine oxide surfactants are preferred. In general, the fatty acid diethanolamides and N-alkyl dimethylamine oxides are preferred for use in the compositions. Especially preferred are the fatty acid diethanolamides and N-alkyl dimethylamine oxides where the fatty hydrocarbon chain contains from 10 to 18 carbon atoms. For example, especially preferred nonionic surfactants include lauric acid diethanolamide, N-lauryl dimethylamine oxide, coconut acid diethanolamide, myristic acid diethanolamide, and oleic acid diethanolamide.

Additional categories of surfactant materials may also be included such as cationic and zwitterionic surfactants, and representative compounds are set forth in detail in U.S. Pat. No. 4,902,499, issued Feb. 20, 1990, which is considered to be incorporated herein by reference.

Other adjuvants may be added to the compositions of this invention such as thickeners, perfumes, colorants, electrolytes, pH control ingredients, foam boosters and foam stabilizers, antimicrobials, antioxidants, ultraviolet light absorbers and medicaments. For example, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps or more preferably in the range of 1000 to 4000 cps as measured at 25° C. are usually suitable.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as sodium or ammonium chloride, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention.

The perfumes which can be used in the compositions are the cosmetically acceptable perfumes. Colorants are used to confer a color to the composition and may generally be used. Although not required, it is preferred to employ an acid to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid.

If for special purposes conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallylammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,ω-bis-(triethanol-ammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers. Other categories of conditioners may also be employed.

A preservative may be required and representative preservatives which may be employed include about 0.1-0.2 weight percent of compounds such as formaldehyde, dimethyloldimethylhydantoin, 5-bromo-5-nitro-1,3-dioxane, methyl-and propyl para-hydroxybenzoates, and mixtures of such benzoates with sodium dehydroacetate, sorbic acid, and imidazolidinyl urea.

The compositions of the present invention may also be formulated to include dyes, colorants, reducing agents, neutralizing agents, and preservatives, necessary for their application as permanent wave systems or hair dyes, for example. The active formulation can be applied in several different forms including lotions, gels, mousses, aerosols, and pump sprays, for example, and as conditioners and shampoos. The active ingredient may include a carrier, and suitable carrier fluids for hair care formulations are water as well as, for example, such fluids as alcohols namely ethanol or isopropanol, hydrocarbons and halogenated hydrocarbons as mineral spirits and trichloroethane, cyclic siloxanes, and aerosol propellants.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

In some instances, it may be beneficial to include a methylsiloxane fluid corresponding to the average unit formula $(CH_3)_aSiO_{(4-a/2)}$ wherein a is an integer having an average value of from two to three. The methylsiloxane fluid comprises siloxane units joined by Si-O-Si bonds. Representative units are $(CH_3)_3SiO_{\frac{1}{2}}$, $(CH_3)_2SiO_{2/2}$, $(CH_3)SiO_{3/2}$, and $SiO_{4/2}$. These units are present in such molar amounts so that there is an average of from about two to three methyl groups per silicon atom in the methylsiloxane fluid, and the fluid has a viscosity of less than about one hundred centistokes measured at twenty-five degrees Centigrade.

Preferably, the methylsiloxane fluid contains dimethylsiloxane units and optionally trimethylsiloxane units. Of particular utility are methylsiloxane fluids having a viscosity of less than about ten centistokes such as cyclopolysiloxanes of the general formula $[(CH_3)_2SiO]_x$ and linear siloxanes of the general formula $(CH_3)_3SiO[(CH_3)_2SiO]_ySi(CH_3)_3$ in which x is an integer having a value of from three to ten and y is an integer having a value of from zero to about four.

Thus, the low viscosity methylsilicone fluid contemplated in accordance with the present invention includes methylsiloxane fluids representative of which are volatile cyclic silicone fluids and volatile linear silicone fluids. Specific examples of these volatile methylsiloxane fluids are polydimethylcyclosiloxane and the linear silicone fluid hexamethyldisiloxane. Such volatile fluids have viscosities generally less than about ten centistokes measured at twenty-five degrees Centigrade and most preferably have viscosities between about 0.65 to 5.0 centistokes.

The volatile cyclic silicones generally conform to the formula $(R_2SiO)_x$ in which R is an alkyl radical having from one to three carbon atoms or a phenyl group. Most typically the cyclic siloxanes have the formula $[(CH_3)_2SiO]_x$ in which x is an integer from three to ten. Some representative volatile cyclic siloxane compounds found to be especially useful in accordance with the present invention are the methylsiloxane tetramer octamethylcyclotetrasiloxane and the methylsiloxane pentamer decamethylcyclopentasiloxane. Mixtures of the tetramer and pentamer may also be employed. Such cyclic siloxanes have viscosities ranging from about 2.5 centistokes to about five centistokes. These materials are also known under The Cosmetics, Toiletries and Fragrance Association, Inc. monographic designation as cyclomethicone.

The volatile low viscosity linear methylsilicone fluid has the formula $R_3SiO(R_2SiO)_nSiR_3$ in which R is an alkyl radical having one to six carbon atoms and n is an integer of from two to nine. Most representative of this class of volatile linear methylsiloxane fluid is hexamethyldisiloxane of the formula

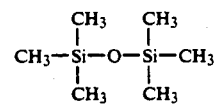

which has a viscosity of 0.65 centistokes measured at twenty-five degrees Centigrade.

Both the cyclic and linear low viscosity volatile methylsiloxane materials are clear fluids and are essentially odorless, nontoxic, nongreasy and nonstinging. Cosmetically these methylsiloxane fluids are nonirritating to the skin and exhibit enhanced spreadability and ease of rub-out when applied to skin tissue. Once applied, the materials will evaporate leaving behind no residue.

The concept of the present invention is illustrated in the following examples and tables in which a shampoo composition is set forth containing 10-80 percent by weight of a volatile carrier such as water; 0.5-5.0 percent by weight of the silicone mixture of a polydiorganosiloxane gum and an amine functional siloxane polymer; 7-35 percent by weight of at least one surfactant; 1-7 percent by weight of a foam booster; less than about two percent by weight of a thickener; and a pH adjusting agent in an amount sufficient to establish a composition pH of between about 5-7. Preferably, the amount of the silicone mixture present in the composition constitutes 5-50 percent by weight of the polydiorganosiloxane gum based on the total weight of the silicone mixture present in the composition.

EXAMPLE I

A control silicone mixture was prepared by combining 160 grams of a polydimethylsiloxane gum and 240 grams of a polydimethylsiloxane fluid having a viscosity of 350 centistokes measured at twenty-five degrees Centigrade. The gum and fluid were mixed with a mechanical stirrer until uniform. This mixture has a viscosity of 1,220,000 centipoise. The control silicone mixture of this example is referred to hereinafter and in the Table as "Silicone 1".

EXAMPLE II

A silicone mixture according to the present invention was prepared by combining 160 grams of a polydimethylsiloxane gum and 240 grams of an amine-modified siloxane having the formula

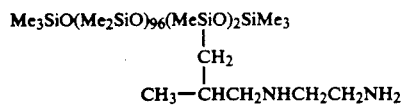

in which Me is methyl. The gum was a high molecular weight silicone and an OH endblocked siloxane containing one hundred mole percent $Me_2SiO$ units. The gum and the amine functional silicone were mixed with a mechanical stirrer until uniform. This mixture has a viscosity of 146,000 centipoise. The silicone mixture of this example is referred to hereinafter and in the Table as "Silicone 2".

The much lower viscosity of silicone mixture "Silicone 2" of the present invention in comparison to the viscosity of the control silicone mixture "Silicone 1" is advantageous and beneficial since it facilitates formulation of the silicone mixture into a shampoo.

EXAMPLE III

Ten shampoo base compositions were prepared containing the various ingredients shown in Table I below. Phases A and B were each prepared separately by mixing together the ingredients in each phase until uniform. Phases A and B were combined, mixed together until uniform, and the pH of the resulting shampoo base composition was adjusted to a pH of 5-7 with citric acid.

TABLE

| Ingredients | SHAMPOO BASE FORMULAS (%) | | | | | | | | | |
|---|---|---|---|---|---|---|---|---|---|---|
|  | 1 | 2 | 3 | 4 | 5 | 6 | 7 | 8 | 9 | 10 |
| PHASE A: |  |  |  |  |  |  |  |  |  |  |
| Ammonium Lauryl Sulfate (30%) | 30.0 | 30.0 | 30.0 | 30.0 | 30.0 | 30.0 | 30.0 | 30.0 | 30.0 | 30.0 |
| Water | 66.5 | 64.5 | 63.0 | 66.0 | 64.5 | 65.0 | 64.5 | 64.0 | 64.0 | 67.0 |
| Ammonium Chloride | — | 1.0 | 1.0 | — | 0.5 | 1.0 | 1.0 | 0.5 | 1.0 | 1.0 |
| Hydroxypropyl methylcellulose | — | — | — | 0.5 | — | — | 0.5 | 1.0 | 1.0 | — |
| PHASE B: |  |  |  |  |  |  |  |  |  |  |
| Cocamide DEA | 3.0 | 4.0 | 5.0 | 3.0 | 4.0 | 3.0 | 3.0 | 3.0 | 3.0 | 3.0 |
| Silicone 1 | — | — | — | — | 0.5 | — | — | — | — | — |
| Silicone 2 | 0.5 | 0.5 | 1.0 | 0.5 | — | 1.0 | 1.0 | 1.5 | 1.0 | — |
| ADDED TO A & B |  |  |  |  |  |  |  |  |  |  |
| Citric Acid | — | 0.5 | 0.5 | 0.5 | 0.5 | 0.5 | 0.5 | 0.5 | 0.5 | 0.5 |
| Stability @ 23° C. (Days) | >42 | >42 | >42 | >42 | <1 | >42 | >42 | >42 | >42 | >42 |

The shelf stability of each shampoo base composition was determined, and as noted in Table I, the stability of the shampoo base compositions 1–4 and 6–10 of the present invention exceeded 42 days, whereas the stability of the shampoo base composition 5 containing the control silicone mixture "Silicone 1" was less than twenty-four hours.

In Table I, ammonium lauryl sulfate was employed as anionic surfactant. Ammonium chloride and hydroxypropyl methylcellulose were used as the thickening agent. The foam booster was a nonionic surfactant Cocamide DEA which is the CTFA adopted name for coconut fatty acid diethanolamide. The volatile carrier was water, and as noted above, citric acid was used as the pH adjusting agent.

EXAMPLE IV

Shampoo base compositions 2 and 10 shown in Table I were tested on hair for conditioning benefits. Shampoo base composition 2 contained silicon mixture "Silicone 2" as indicated in Table I and is representative of the present invention. Shampoo base composition 10 contained no silicone as shown in Table I, and was used as the blank control shampoo. Shampoo base composition 5 containing silicon mixture "Silicone 1" which is not representative of the present invention, could not be tested as it lacked sufficient shelf stability.

Hair tresses were shampooed with a commercial grade shampoo and dried. Each tress was wetted and 0.5 grams of the test shampoo was applied to the tress. The test shampoo was worked into the tress for thirty seconds. The tress was rinsed for thirty seconds with water and detangled by passing the wide part of a comb through the tress one time. The tress was hung to dry and evaluated after the elapse of twenty-four hours. The tress was evaluated for wet and dry combing, and dry feel. Subjective combing evaluations were conducted by volunteers who assigned values to each tress between one and 5, with one being the best and five the worst. The results for shampoo base compositions 2 and 10 are shown in Table II.

TABLE II

| Shampoo Base | Wet Combing | Dry Combing | Dry Feel |
|---|---|---|---|
| 2 | 3.5 | 2.25 | 2.5 |
| 10 | 3.5 | 3.0 | 3.0 |

Table II indicates that the dry hair properties of the compositions in accordance with the present invention are improved due to the incorporation into the composition of the mixture of the silicone gum and the amine functional siloxane. Tables I and II further show that silicone gum/amine functional silicone containing conditioning shampoos according to the present invention are easier to prepare and provide improved conditioning benefits to hair.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A shampoo composition comprising 10–80 percent by weight of a carrier; 0.5–5.0 percent by weight of a mixture of a polydiorganosiloxane gum and an amine functional siloxane polymer; and 7–35 percent by weight of a water soluble anionic surfactant; the polydiorganosiloxane gum having the average unit formula $R_aSiO_{4-a/2}$ in which each R substituent is a monovalent radical selected from the group consisting of a methyl radical, a vinyl radical, a phenyl radical, and a 3,3,3-trifluoropropyl radical, a has an average value of 1.95–2.005 inclusive, at least ninety percent of the total number of R substituents being methyl radicals, the molecules of the polydiorganosiloxane gum being terminated by a substituent selected from the group consisting of silanols, alkoxys, and $R_3SiO_{0.5}$, in which R is the same as defined above; the amine functional siloxane polymer having the formula:

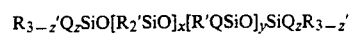

wherein R' denotes an alkyl group of 1 to 4 carbons or a phenyl group with the proviso that at least 50 percent of the total number of R' groups are methyl; Q denotes an amine functional substituent of the formula —R"Z wherein R" is a divalent alkylene radical of 3 to 6 carbon atoms and Z is a monovalent radical selected from the group consisting of —NR$_2$''', and —NR'''(CH$_2$)$_n$NR$_2$'''; wherein R''' denotes hydrogen or an alkyl group of 1 to 4 carbons, R'''' denotes an alkyl group of 1 to 4 carbons, and n is a positive integer having a value of from 2 to 6; z has a value of 0 or 1; x has an average value of 25 to 3000; y has an average value of 0 to 100 when z is 1, y has an average value of 1 to 100 when z is 0; with the proviso that in all cases y has an average value that is not greater than one tenth the average value of x said composition having improved shelf stability and hair conditioning properties as compared to the same composition not containing amine-functional siloxane polymer.

2. The composition according to claim 1 in which the mixture includes 5-50 percent by weight of the polydiorganosiloxane gum (i) based on the total weight of the mixture present in the composition.

3. A method of conditioning hair comprising applying to hair the composition according to claim 1.

4. A method of conditioning hair comprising applying to hair the composition according to claim 2.

* * * * *